(12) United States Patent
Lemonds et al.

(10) Patent No.: US 9,000,211 B2
(45) Date of Patent: Apr. 7, 2015

(54) PROCESS FOR PRODUCTION OF METHACRYLIC ACID ESTER HAVING INCREASED YIELD

(75) Inventors: Andrew M. Lemonds, Schwenksville, PA (US); Jinsuo Xu, Fort Washington, PA (US)

(73) Assignee: Rohm and Haas Company

( * ) Notice: Subject to any disclaimer, the term of this patent is extended or adjusted under 35 U.S.C. 154(b) by 100 days.

(21) Appl. No.: 13/877,388

(22) PCT Filed: Oct. 4, 2011

(86) PCT No.: PCT/US2011/054762
§ 371 (c)(1),
(2), (4) Date: Aug. 30, 2013

(87) PCT Pub. No.: WO2012/047883
PCT Pub. Date: Apr. 12, 2012

(65) Prior Publication Data
US 2013/0338396 A1      Dec. 19, 2013

Related U.S. Application Data

(60) Provisional application No. 61/496,621, filed on Jun. 14, 2011, provisional application No. 61/404,680, filed on Oct. 7, 2010, provisional application No. 61/404,681, filed on Oct. 7, 2010.

(51) Int. Cl.
*C07C 67/20* (2006.01)
*C07C 67/327* (2006.01)

(52) U.S. Cl.
CPC ............... *C07C 67/327* (2013.01); *C07C 67/20* (2013.01)

(58) Field of Classification Search
CPC .................................. C07C 67/20; C07C 67/22
See application file for complete search history.

(56) References Cited

U.S. PATENT DOCUMENTS

| | | | | |
|---|---|---|---|---|
| 5,068,399 A | * | 11/1991 | Naito et al. | .................. 560/212 |
| 5,087,736 A | | 2/1992 | Higuchi et al. | |
| 5,250,729 A | | 10/1993 | Abe et al. | |
| 5,304,656 A | | 4/1994 | Yano et al. | |
| 5,393,918 A | * | 2/1995 | Dobson | .......................... 560/215 |
| 8,183,406 B2 | | 5/2012 | Lemonds et al. | |
| 2002/0055650 A1 | | 5/2002 | Hidaka et al. | |

FOREIGN PATENT DOCUMENTS

| FR | 2064583 | 9/1969 |
|---|---|---|
| GB | 1256288 | 2/1972 |

OTHER PUBLICATIONS

Lee, Arstechnica.com, Single Atom Catalyst Suggests We Don't Understand Catalysis that Well, 2013, pp. 1-4, recovered from: http://arstechnica .com/science/2013/11/single-atom-catalyst-suggests-we-dont-understand-catalysis-that-well/ on Sep. 10, 2014.*
White et al, Basic Energy Sciences Advisory Committee Subpanel Workshop Report, Opportunities for Catalysis in the 21st Century, 2002, pp. 1-47.*
Yang et al, ACS Catalysis, Understanding the Optimal Adsorption Energies for Catalyst Screening in Heterogeneous Catalysis, 2014, 4, pp. 182-186.*
Wikipedia , Wikipedia, Francium, 2014, recovered from: http://en.wikipedia.org/wiki/Francium on Sep. 10, 2014.*

* cited by examiner

*Primary Examiner* — Paul A Zucker

(57) ABSTRACT

This invention provides a method for producing α,β-unsaturated carboxylic acid esters in high yield from acetone cyanohydrin and sulfuric acid through the separation and concurrent catalytic conversion of reaction side products to additional α,β-unsaturated carboxylic acid ester product. The catalyst comprises at least one Group IA element and may include a porous support and/or a promoter element selected from at least one of phosphorous, boron, titanium, zinc, zirconium, tin, bismuth, cerium, and alkaline earth metals. The method for producing methacrylic acid esters, such as methylmethacrylate (MMA), comprises the steps of: i) providing an alkyl alcohol and an organic traction comprising an alkyl methacrylate, an alkyl α-hydroxyisobutyrate and an alkoxyisobutyrate; ii) vaporizing at least a portion of the organic fraction and at least a portion of the alkyl alcohol; iii) contacting the vaporized organic fraction and alcohol with a catalyst comprising at least one element selected from the group consisting of lithium, sodium, potassium, rubidium, cesium and francium, to convert the alkyl ahydroxyisobutyrate and alkyl alkoxyisobutyrate to additional alkyl methacrylate and produce a mixture comprising alkyl methacrylate, methacrylic acid, alkyl alcohol, and water.

20 Claims, 6 Drawing Sheets

MMA yield (Yres) from direct catalytic treatment of MMA purification residue over different catalysts MMA yield from direct catalytic treatment of MMA purification residue over 10% $Cs_2O/SiO_2$ (Davisil® 636)

MMA yield and flash vapor recovery

- ◆ Yres
- ■ Yflash
- ▲ Flash vapor fraction (g distillate/100g residue)

PROCESS FOR PRODUCTION OF METHACRYLIC ACID ESTER HAVING INCREASED YIELD

CROSS-REFERENCE TO RELATED APPLICATIONS

This application claims priority from U.S. provisional application Ser. No. 61/496,621, filed Jun. 14, 2011, U.S. provisional application Ser. No. 61/404,680, filed Oct. 7, 2010, U.S. provisional application Ser. No. 61/404,681, filed Oct. 7, 2010, which are incorporated herein by reference in their entirety.

FIELD OF THE INVENTION

This invention relates to a process for producing α-, β-unsaturated carboxylic acid esters from acetone cyanohydrin and sulfuric acid.

BACKGROUND OF THE INVENTION

This invention relates to a process for producing high purity methacrylic acid esters in increased yield compared to conventional processes. A number of commercial processes are practiced for the production of such esters including sulfuric acid treatment of acetone cyanohydrin, two stage oxidation of isobutylene or t-butyl alcohol, and liquid phase catalytic condensation of propionaldehyde with formaldehyde.

U.S. Pat. No. 4,529,816 describes a conventional acetone cyanohydrin ("ACH") process for the production of methyl methacrylate ("MMA") from ACH. In this process, ACH is hydrolyzed by sulfuric acid to produce α-hydroxyisobutyramide ("HIBAM") and α-sulfatoisobutyramide ("SIBAM"). Next, the HIBAM and SIBAM are thermally converted to 2-methacrylamide ("MAM") and a small amount of methacrylic acid ("MAA"). The MAM is esterified with methanol to produce the desired MMA product, while residual HIBAM is esterified to methyl α-hydroxyisobutyrate ("α-MOB"). The esterification product stream is a mixed product that is subjected to separation and purification steps to isolate the MMA product from the other compounds. Typically, a purified MMA product stream is produced, along with a purification residue comprising other compounds including, but not limited to, α-MOB and methyl β-methoxyisobutyrate (β-MEMOB). The recovery and conversion of one or more of these other compounds to produce additional MMA product has been the subject of various research and development efforts having varying degrees of success and practical utility. In particular, U.S. Pat. No. 4,529,816 describes an improvement wherein the α-MOB is isolated and recycled to the process between the thermal conversion and esterification steps.

U.S. Pat. No. 5,393,918 describes a process similar to that of U.S. Pat. No. 4,529,816, but the thermal conversion step is eliminated. Instead, the hydrolysis product is subjected directly to esterification with methanol to produce an esterification product that includes the desired MMA product, as well as α-MOB and β-MEMOB. In the process described in U.S. Pat. No. 5,393,918, the esterification ("crude MMA") product is subjected to distillation to recover the product MMA and produces a liquid residue stream comprising α-MOB and β-MEMOB. The α-MOB and β-MEMOB are separated from the residue stream, typically by fractional distillation. The recovered α-MOB and β-MEMOB are subjected to vapor phase catalytic dehydration, using a crystalline aluminosilicate, to produce a recycle mixture comprising MMA, methacrylic acid ("MAA"), methanol and water, which is recycled to the process between the hydrolysis and esterification steps, or between the esterification and separation steps. The dehydration of α-MOB and β-MEMOB is performed in the vapor phase and in the presence of a crystalline aluminosilicate catalyst, which may or may not be promoted with an alkali metal or a platinum group element.

U.S. Pat. No. 5,087,736 discloses an ACH process that does not require sulfuric acid for preparing methacrylic acid esters. A key step of this process is the vapor phase dehydration of α-MOB in the presence of an alkali metal and platinum group element modified crystalline aluminosilicate, as disclosed in U.S. Pat. No. 5,068,399. However, this process suffers from low yields based on ACH.

FR 2064583 and GB 1256288 disclose purifications of a crude MMA product stream to produce a residual bottoms stream containing α-MOB and MAA, both of which are then converted to MMA by treatment with sulfuric acid and methanol, respectively and concurrently. The conversion of α-MOB and MAA is performed separate and apart from the hydrolysis and esterification reaction steps of the conventional MMA process and is followed by distillation to recover the MMA produced.

A variety of solid catalysts have been used for converting α-MOB and/or β-MEMOB into MMA and MAA in the vapor phase. For example, in Japanese Patent Publication Nos. 20611/1969, 20612/1969 and 15724/1970, a phosphate-based acid or salt deposited onto silica or silica-alumina was used. These technologies were plagued by the need for very high reaction temperatures, unacceptable levels of by-product methyl isobutyrate (MIB) formation, and fast deactivation by coke deposition. Crystalline aluminosilicates containing alkali or alkaline earth metals have been thoroughly studied for the conversion of α-MOB and β-MEMOB into MMA and MAA, as disclosed in U.S. Pat. No. 5,371,273, U.S. Pat. No. 5,393,918, and U.S. Pat. No. 5,739,379, as well as JP Application No. 65896/1990, U.S. Pat. No. 5,250,729 and EP 429,800 A2. The dehydration of α-MOB to MMA was commercialized by the Mitsubishi Gas Chemical Company in 1997 as a sulfuric acid-free ACH-based MMA process. The art shows that crystalline aluminosilicates such as zeolite NaX are well suited for α-MOB dehydration; however, they are limited in their ability to achieve simultaneous high yields on α-MOB and β-MEMOB and, therefore, have limited applicability for MMA residue yield recovery.

Catalysts containing Cs and silica gels have been explored for a number of reactions, including dehydrations, aldol condensations and Michael additions, but not conversion of α-MOB and/or β-MEMOB into MMA and MAA in the vapor phase. U.S. Pat. No. 4,841,060, U.S. Pat. No. 5,625,076, and U.S. Pat. No. 5,304,656, for example, disclose catalysts containing silicon and at least one element selected from the group consisting of alkali metals and alkaline earth metals for intramolecular dehydrations, such as the conversion of mercaptoalkanols to alkylene sulfides, alkanolamines to cyclic amines, N-(2-hydroxyethyl)-2-pyrrolidone to N-vinyl-2-pyrrolidone, and tertiary N-(2-hydroxyalkyl) carboxylic acid amide to tertiary N-alkenyl carboxylic acid amide. The substrates and reactions involved in these processes, however, differ chemically from dehydration and demethanolation of α-MOB and β-MEMOB, respectively, to MMA.

SUMMARY OF THE INVENTION

The present invention is a method for producing α-, β-unsaturated carboxylic acid esters in high yield through recovery and conversion of process intermediates. In one embodiment, the invention is a method for producing methacrylic acid esters comprising the steps:

providing a $C_1$-$C_{12}$ alkyl alcohol and an organic fraction comprising $C_1$-$C_{12}$ alkyl methacrylate, $C_1$-$C_{12}$ alkyl α-hydroxyisobutyrate and $C_1$-$C_{12}$ alkyl β-$C_1$-$C_{12}$ alkoxyisobutyrate;

vaporizing at least a portion of the organic fraction and at least a portion of the $C_1$-$C_{12}$ alkyl alcohol;

contacting the vaporized organic fraction and alcohol with a catalyst comprising at least one element selected from the group consisting of lithium, sodium, potassium, rubidium, cesium and francium, to convert the $C_1$-$C_{12}$ alkyl α-hydroxyisobutyrate and $C_1$-$C_{12}$ alkyl β-$C_1$-$C_{12}$ alkoxyisobutyrate to additional $C_1$-$C_{12}$ alkyl methacrylate and produce a converted mixture that comprises a $C_1$-$C_{12}$ alkyl methacrylate, methacrylic acid, $C_1$-$C_{12}$ alkyl alcohol, and water.

It has surprisingly been found that the other by-products and compounds present in the organic fraction do not substantially interfere with the activity of the catalyst in the vapor phase. In addition, it has been surprisingly found that the catalyst employed in the present invention successfully facilitates the concurrent conversion of $C_1$-$C_{12}$ alkyl α-hydroxyisobutyrate and $C_1$-$C_{12}$ alkyl β-$C_1$-$C_{12}$ alkoxyisobutyrate to additional $C_1$-$C_{12}$ alkyl methacrylate product.

In addition, the capability of the catalyst to simultaneously convert additional by-product species, such as MAA and $C_1$-$C_{12}$ alkyl β-hydroxyisobutyrate, to $C_1$-$C_{12}$ alkyl methacrylate product is unexpected.

In another embodiment, the organic fraction is produced by a process comprising the following steps, which precede the 3 steps set out hereinabove:

hydrolyzing ACH with sulfuric acid to produce a hydrolysis mixture comprising 2-methacrylamide, α-sulfatoisobutyramide, α-hydroxyisobutyramide, and methacrylic acid;

esterifying the hydrolysis mixture with a $C_1$-$C_{12}$ alkyl alcohol to produce an esterification mixture comprising a $C_1$-$C_{12}$ alkyl methacrylate, a $C_1$-$C_{12}$ alkyl α-hydroxyisobutyrate, and a $C_1$-$C_{12}$ alkyl β-$C_1$-$C_{12}$ alkoxyisobutyrate;

separating the esterification mixture into an aqueous fraction and an organic fraction comprising $C_1$-$C_{12}$ alkyl methacrylate, the $C_1$-$C_{12}$ alkyl α-hydroxyisobutyrate and the $C_1$-$C_{12}$ alkyl β-$C_1$-$C_{12}$ alkoxyisobutyrate.

DETAILED DESCRIPTION OF THE INVENTION

Figure 1:
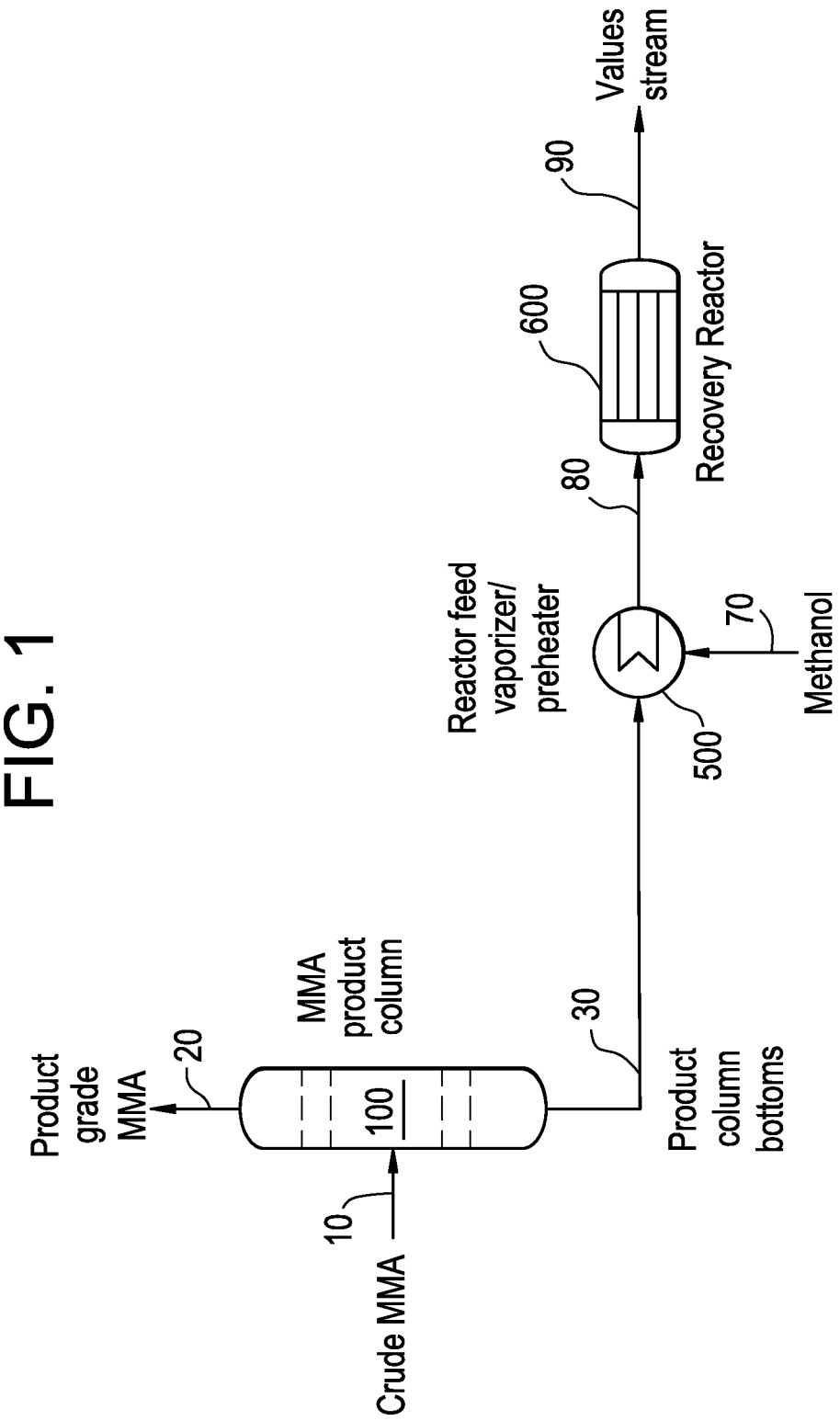
FIG. 1 is a schematic diagram of one embodiment of the process of the invention.

The recovery process of the invention converts certain by-product species to MMA. For example, a stream enriched in by-products is obtained by distillation of a residue stream and is subjected to the vapor phase catalytic reaction process described herein. In one embodiment, the invention is a process for producing high purity α, β-unsaturated carboxylic acid esters in high yield, based on the starting ACH. The purity of the ester product preferably is greater than about 99 weight percent, although less pure products can be obtained from the process if desired. The yield of product esters from the process preferably is greater than about 95 percent, based on the starting ACH. In one embodiment of the invention, the yield is at least 2, preferably at least 4, percent higher than that of a prior art process having no post-reactor containing the catalyst employed in the inventive process.

In one embodiment of the invention, the inventive process involves the following steps:

(a) Hydrolyze ACH with sulfuric acid to produce a hydrolysis mixture comprising 2-methacrylamide, α-sulfatoisobutyramide, α-hydroxyisobutyramide, and methacrylic acid;

(b) Esterify the hydrolysis mixture with a $C_1$-$C_{12}$ alkyl alcohol to produce an esterification mixture comprising a $C_1$-$C_{12}$ alkyl methacrylate, a $C_1$-$C_{12}$ alkyl α-hydroxyisobutyrate and $C_1$-$C_{12}$ alkyl β-$C_1$-$C_{12}$ alkoxyisobutyrate;

(c) Separate the esterification mixture into an aqueous fraction and an organic fraction comprising $C_1$-$C_{12}$ alkyl methacrylate, $C_1$-$C_{12}$ alkyl α-hydroxyisobutyrate and $C_1$-$C_{12}$ alkyl β-$C_1$-$C_{12}$ alkoxyisobutyrate;

(d) Provide a $C_1$-$C_{12}$ alkyl alcohol co-feed (which may or may not be the same alcohol as the $C_1$-$C_{12}$ alkyl alcohol used in the esterifying step (b));

(e) Vaporize the co-feed and at least a portion of the organic fraction to produce a vapor feed stream; and (f) Contact the vapor feed stream with a catalyst comprising at least one element selected from the group consisting of lithium, sodium, potassium, rubidium, cesium and francium, to convert the $C_1$-$C_{12}$ alkyl α-hydroxyisobutyrate and $C_1$-$C_{12}$ alkyl β-$C_1$-$C_{12}$ alkoxyisobutyrate to additional $C_1$-$C_{12}$ alkyl methacrylate to a converted mixture comprising the $C_1$-$C_{12}$ alkyl methacrylate, methacrylic acid, $C_1$-$C_{12}$ alkyl alcohol, and water. The converted mixture may be wholly or partially recycled.

In one embodiment of the invention, the HIBAM concentration in the process stream just prior to esterification is from about 2 to about 20 mole % based on the starting ACH. In one embodiment of the invention, the SIBAM concentration in the process stream just prior to esterification is from about 1 to about 20 mole % based on the starting ACH.

It is noted that the conversion that occurs during the contacting step, e.g. step (f), involves concurrent dehydration of $C_1$-$C_{12}$ alkyl α-hydroxyisobutyrate to additional $C_1$-$C_{12}$ alkyl methacrylate and demethanolation of $C_1$-$C_{12}$ alkyl β-$C_1$-$C_{12}$ alkoxyisobutyrate to additional $C_1$-$C_{12}$ alkyl methacrylate. Thus, by-products are recovered and simultaneously converted to additional desired $C_1$-$C_{12}$ alkyl methacrylate product. The process of the invention involves conversion of the by-products prior to recycling to the process, and in the process a greater portion of the recovered by-products can be converted, compared to previously practiced processes.

The recovery process of the invention converts distillation residue species to MMA. The organic fraction of the separation step, e.g. step (c), at a minimum, comprises $C_1$-$C_{12}$ alkyl methacrylate, $C_1$-$C_{12}$ alkyl α-hydroxyisobutyrate and $C_1$-$C_{12}$ alkyl β-$C_1$-$C_{12}$ alkoxyisobutyrate. For example, the $C_1$-$C_{12}$ alkyl methacrylate may be MMA, the $C_1$-$C_{12}$ alkyl α-hydroxyisobutyrate may be α-MOB, the $C_1$-$C_{12}$ alkyl β-$C_1$-$C_{12}$ alkoxyisobutyrate may be β-MEMOB, and in this case the organic fraction comprises the MMA, α-MOB and β-MEMOB. The organic fraction may also comprise organic acids such as, for example, MAA.

Depending on the configuration of the process equipment, the organic fraction may contain varying amounts of $C_1$-$C_{12}$ alkyl methacrylate. For example, in the embodiment depicted in FIG. 1, the portion of the organic fraction, stream 30, fed to the vaporizer may comprise, for example, from 20 to 70 weight percent of $C_1$-$C_{12}$ alkyl methacrylate. In the embodiment depicted in FIG. 2, the portion of the organic fraction, stream 40, fed to the vaporizer may comprise, for example, from 0 to 5 weight percent of $C_1$-$C_{12}$ alkyl methacrylate. Finally, in the embodiment depicted in FIG. 3, the portion of the organic fraction, stream 60, fed to the vaporizer may comprise, for example, from 0 to 10 weight percent of $C_1$-$C_{12}$ alkyl methacrylate.

The co-feed $C_1$-$C_{12}$ alkyl alcohol preferably is methanol. Advantageously, the alcohol is employed in an amount sufficient to maintain a relatively high ratio of MMA to MAA in the reactor product stream. Preferably, the weight ratio of co-feed to organic fraction fed to the reactor is from 0.2 to 2.

For illustrative purposes, the following description will focus on a method for producing methyl methacrylate (MMA) as the $C_1$-$C_{12}$ alkyl methacrylate. However, as will be readily recognized by persons of ordinary skill in the relevant art, the method of the present invention is applicable to preparation of methacrylic acid esters via the sulfuric acid/ACH process and esterification with $C_1$-$C_{12}$ alkyl alcohols. Generally, use of alcohols of $C_1$-$C_4$, such as any of methanol, ethanol, n-propanol, isopropanol, n-butanol, and isobutanol, is most common because of the commercial value of the resulting methacrylate esters. Methanol is the preferred alcohol.

Figure 2:
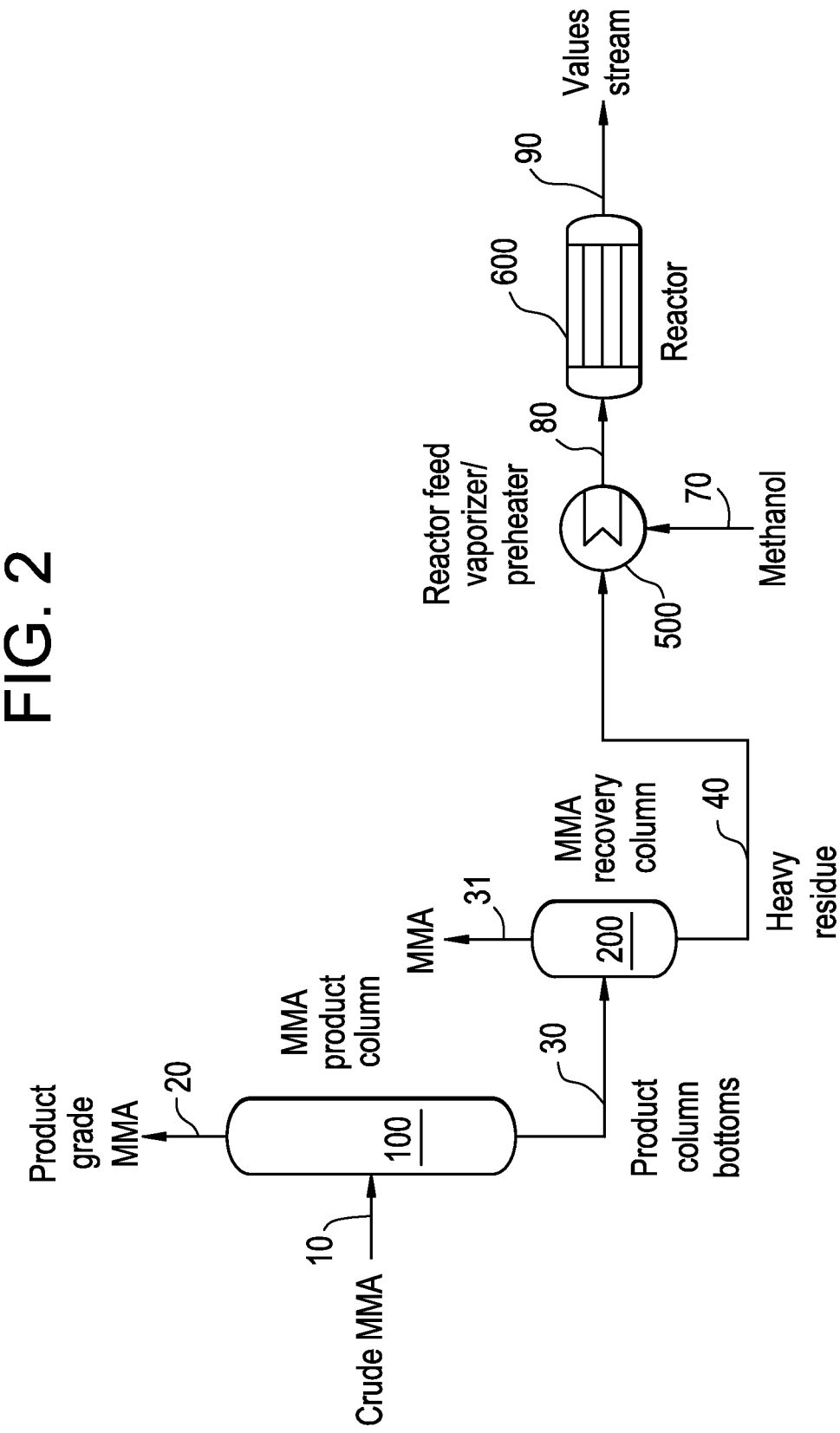
FIG. 2 is a schematic diagram of one embodiment of the process of the invention.
Figure 3:
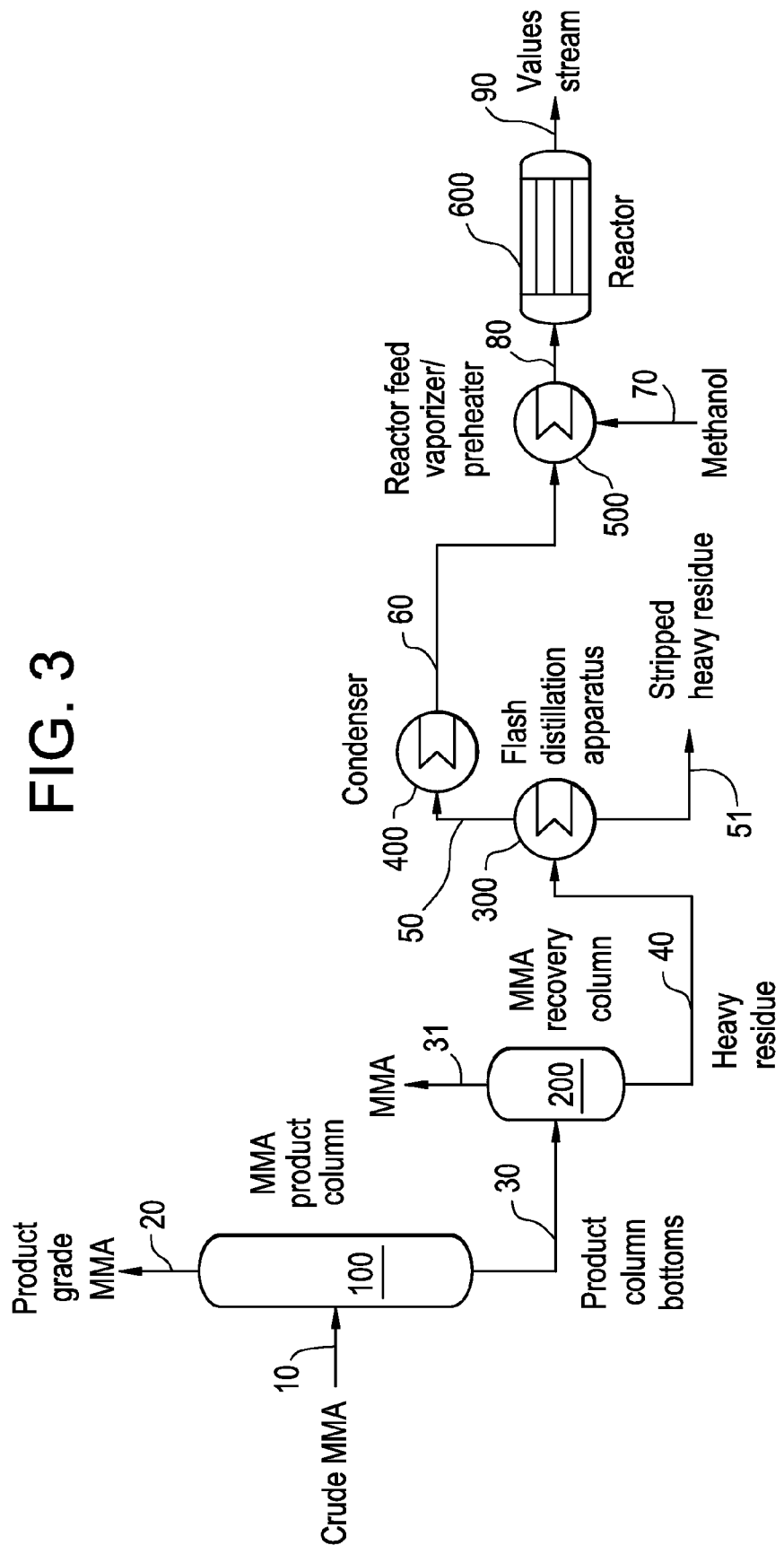
FIG. 3 is a schematic diagram of one embodiment of the process of the invention.

The process of the invention can be further described by reference to the production of MMA as depicted in FIGS. 1-3. One embodiment of the invention is represented by FIG. 1. A crude MMA stream 10 is obtained by the conventional ACH route to MMA and comprises a mixture of MMA and heavy ends. Crude MMA stream 10 is distilled in MMA product column 100 under conventional conditions known to those skilled in the art, to yield a high purity, product grade MMA distillate 20 and an MMA product column bottoms stream 30 comprising the heavy ends and some residual MMA. For example, the MMA product column bottoms stream 30 may contain about 50 wt. % MMA and about 50 wt. % heavy ends. According to this embodiment, the MMA product column bottoms stream 30 is the portion of the organic fraction that is vaporized in vaporizer 500 together with methanol from stream 70. In the process of FIG. 1, the vaporizer 500 effluent stream comprising vaporized MMA product column bottoms stream and vaporized methanol is fed to recovery reactor 600, wherein α-MOB, β-MEMOB, MAA, and methyl β-hydroxyisobutyrate (β-MOB) present in the product column bottoms stream 30 are converted to MMA found in values stream 90.

Another embodiment of the invention is represented in FIG. 2. The process of FIG. 2 is similar to that of FIG. 1, except that the MMA product column bottoms stream 30 is further distilled in MMA recovery column 200 to remove overhead a substantial amount of the residual MMA, yielding a heavy residue stream 40. The heavy residue stream is substantially depleted in MMA. For example, it may contain 5 wt. % or less MMA. The heavy residue stream is vaporized in vaporizer 500. Thus, the heavy residue stream is the portion of the organic fraction that is vaporized in vaporizer 500 together with the methanol of stream 70. According to this embodiment, the vaporizer 500 effluent stream 80 comprising the vaporized heavy residue stream and vaporized methanol are fed to the recovery reactor 600, wherein α-MOB, β-MEMOB, MAA, and β-MOB are converted to a converted mixture comprising MMA, which mixture is discharged from the reactor in values stream 90.

FIG. 3 depicts another embodiment of the invention. The process of FIG. 3 is similar to that of FIG. 2, except that the heavy residue stream 40 is fed to a flash distillation apparatus 300. For example, 50 to 80 wt. % of the heavy residue stream 40 is evaporated in flash distillation apparatus 300, while the remainder exits apparatus 300 in the liquid phase stripped heavy residue stream 51, which can be processed further or treated as waste or fuel. When the flash distillation is conducted under vacuum, e.g. at 3.33 to 6.67 kPa (25 to 50 mmHg absolute), the flash temperature preferably is in the range of 120 to 150° C. The flash evaporated heavies 50 are then condensed in condenser 400 and the condensed heavies stream 60 is subsequently vaporized in vaporizer 500, then fed, as a co-feed with vaporized methanol, to the recovery reactor 600, wherein α-MOB, β-MEMOB, MAA, and β-MOB are converted to MMA, which is discharged from the reactor in values stream 90. Thus, stream 60 is the portion of the organic fraction that is vaporized in vaporizer 500 for the embodiment shown in FIG. 3. For this embodiment, the flash distillation apparatus advantageously is operated at or below, preferably at, a temperature beyond which incremental MMA recovery is not achieved or is negligible.

An alternative embodiment to that of the previous paragraph involves sending flash evaporated heavies 50 to the recovery reactor 600, without passing the heavies 50 through condenser 400. The heavies 50 may be sent to reactor 600 either with or without sending them through vaporizer 500. It is possible in this embodiment to replace to replace condenser 400 with a compressor (not shown) to transfer the flash evaporated heavies vapor stream 50 to vaporizer 500. Operating conditions for these embodiments can be readily determined by those skilled in the art.

In one embodiment of the present invention, ACH is hydrolyzed using excess sulfuric acid at a temperature from about 80° C. to about 135° C., preferably from about 80° C. to about 105° C., for a time sufficient to maximize the pre-esterification yield of the total of MAM, SIBAM, HIBAM, and MAA. The temperature can be maintained at a single value or changed during the course of the reaction. This may be accomplished either continuously or stepwise. The time required will vary from less than 1 minute to about 60 minutes and a hydrolysis mixture will be produced comprising MAM, SIBAM, HIBAM, and MAA. Sulfuric acid solution concentrations of 95-100% or more are preferred, but 100% or higher, e.g. oleum, sulfuric acid is not required. The mole percent distribution of reacted ACH equivalent products in the resulting hydrolysis mixture will vary. However, conditions are preferred that result in the following composition: about 60-80% MAM; about 1-20% SIBAM; about 2-20% HIBAM (more preferably 5-15%); and about 0-5% MAA with an overall ACH conversion rate of about 100%. One advantage of this embodiment is that the yield loss is reduced compared to losses incurred in the conventional process by efforts to reduce HIBAM levels during thermal conversion to MAM.

In one embodiment of the invention, the process is similar to the process of FIG. 3, except that flash distillation apparatus 300 is replaced by multistage fractional distillation apparatus 310 (not shown). For example, 40 to 60 wt. % of the heavy residue stream 40 is distilled in a fractional distillation apparatus 310, while the remainder that contains MAA, MAM and others exits apparatus 310 in the liquid phase stripped heavy residue stream 51, which can be processed further or treated as waste or fuel. The distillation in apparatus 310 is preferably, but not limited to, a multi-stage, vacuum distillation, which may be conducted batchwise or continuously. For example, a suitable continuous distillation method comprises vacuum distilling using a 10 to 30 tray tower, where the reboiler pressure is in the range of 25 to 200 Torr (3.33 to 26.66 kPa). Preferably, the reboiler pressure is about 150 Torr (20.0 kPa) or less and, depending on the bottoms composition, a reboiler temperature of 150° C. or less is obtained. The distillate-to-feed (D/F) and reflux (L/D) ratios are selected based on the feed composition and desired species recoveries according to methods known to those skilled in the art. Representative D/F and L/D ratios are, respectively, from 0.2 to 0.6 and from 0.4 to 1.0. For this embodiment, the fractional distillation apparatus 310 preferably is operated at a temperature such that heavies such as MAA and MAM do not get into the distillate stream 50.

The use of a polymerization inhibitor in the column is desirable to prevent thermally-induced polymerization of present olefinic species. Many polymerization inhibitors are known to those skilled in the art. Combinations of inhibitors can be employed. An example of an effective inhibitor is phenothiazine (PTZ), which can be introduced at the top of the column. The inhibitor may be delivered in any suitable fashion such as, for example, as a solution in MMA, in a composition similar to the distillate, or in a fraction of the distillate itself. An effective inhibitor level provides about 150 ppm PTZ in the column bottoms stream 51. When using other inhibitors, different concentrations may be required, as is known to those skilled in the art. The distillation overhead stream 50 is then fed to condenser 400 and the process continues as shown in FIG. 3.

Optionally, the method of the present invention may include the aforementioned thermal conversion step after the hydrolyzing step and prior to the esterifying step, wherein at least a portion of the HIBAM in the hydrolysis mixture is converted to MAM, and the resulting cracked hydrolysis mixture is provided to the esterifying step. When practiced, the thermal conversion step comprises heating the hydrolysis mixture to between 90° C. and 160° C. to convert the HIBAM and SIBAM to MAM and produce the cracked hydrolysis mixture that comprises less HIBAM and more MAM than the original hydrolysis mixture.

The present invention renders the thermal conversion step of the old conventional ACH process optional. The typically harsh conditions needed to maximize the MAM yield in the thermal conversion step also served to reduce the overall yield of the process due to side reactions such as, for example, the decomposition of MAM and any MAA, or the dimerization of MAM, and the like. By reducing the severity of the thermal conversion conditions, the yield of MAM may also be reduced due to the lower conversion of SIBAM and HIBAM to MAM. However, in subsequent steps of the method of the present invention, any excess SIBAM and HIBAM is esterified into α-MOB, which is then concurrently converted in the presence of the above-described catalyst to additional MMA. Regardless of whether thermal conversion is employed, additional MMA is produced and recycled to the process, providing an overall increase in the yield of MMA from the process as well as a reduction of waste material that must be disposed of by incineration, landfilling, or the like.

The hydrolysis mixture (uncracked or cracked), comprising MAM, SIBAM, HIBAM and MAA, is esterified using any suitable esterification procedure, such as, for example, the industrial process comprising mixing with excess aqueous $C_1$-$C_{12}$ alkyl alcohol, using sulfuric acid as a catalyst under pressures of up to 791 kPa (100 psig) at 100° C.-150° C., with residence times of generally less than 1 hour. In the case of MMA production, excess aqueous methanol is combined with the hydrolysis mixture. Esterification conditions are not critical and can be varied over a wide range. The only requirement is that the conditions be mild enough such that side reactions (e.g., dimethyl ether formation) and degradation products do not occur to an unacceptable extent.

The esterifying step produces an esterification mixture comprising MMA, α-MOB, and β-MEMOB along with significant quantities of water and unreacted methanol. The esterification mixture may also include other compounds, such as MAA and β-MOB. This mixture is subjected to one or more separation and/or purification steps, comprising the use of one or more distillation columns, to remove excess methanol, water, and light impurities, such as, without limitation, dimethyl ether. Generally, in accordance with the present invention, liquid bottoms residue from at least one of the aforementioned distillation steps is further separated into an aqueous fraction and an organic fraction. For example, without limitation, fractional distillation conditions may be adjusted in a first distillation column to give a forerun of low boiling components such as water, unreacted methanol, small amounts of MMA, and the like and a bottoms stream rich in MMA and other higher boiling components such as α-MOB and β-MEMOB. Furthermore, the bottoms stream may be subjected to one or more further fractional distillation steps to produce a product grade MMA stream, e.g. stream 20, and a product column bottoms stream, e.g. stream 30, comprising MMA, as well as α-MOB, β-MEMOB, MAM, MAA, etc.

At least a portion of the organic fraction is then subjected to vaporization, along with a $C_1$-$C_{12}$ alkyl alcohol co-feed, such as, for example, without limitation, by a vaporizer, to produce a vapor feed stream comprising MMA, α-MOB, and β-MEMOB. The $C_1$-$C_{12}$ alkyl alcohol of the co-feed may be the same or different from the $C_1$-$C_{12}$ alkyl alcohol introduced in the esterifying step.

In particular, among the various fractions produced by the separation steps, at least one organic fraction comprising high purity MMA is obtained. This is a high purity MMA product-grade stream, whereas the remaining residue from this separation step is typically subjected to one or more further separation steps, e.g. as shown in FIGS. 2 and 3, to obtain at least one organic fraction reduced in MMA content compared to the product stream. The organic fraction is then catalytically treated. The operating conditions suitable to effect such separations in the context of the method of the present invention are well within the ability of persons of ordinary skill in the relevant art.

The process of obtaining the organic fraction typically includes a series of distillations wherein a crude MMA stream is obtained and refined by distilling overhead a purified, product-grade MMA stream. From this final product-grade distillation, a residue stream containing heavy ends results, which can be subjected to the recovery and catalytic conversion steps of the method in accordance with the present invention. This residue stream can be then vaporized to yield the vapor feed stream comprising residual MMA, α-MOB, β-MOB β-MEMOB, and MAA.

The vaporization step, involving vaporizing co-feed and at least a portion of the organic fraction, is accomplished by vaporizing, together or separately, the co-feed and at least a portion of the organic fraction. The vaporization may be performed in any apparatus suitable for vaporizing process streams comprising the constituents discussed hereinabove including, but not limited to, flash drums, shell-and-tube heat exchangers, plate-and-frame heat exchangers, natural or forced circulation evaporators, wiped film evaporators, or combinations thereof. In one embodiment of the invention, the vaporized stream is raised to the reaction temperature in the vaporizer. Suitable, but not limiting, conditions include operating pressures and temperatures in the respective ranges of 101 to 506 kPa absolute (1 to 5 atm) and 100 to 400° C. Preferably the pressure will be from 101 to 152 kPa absolute (1 to 1.5 atm) and the temperature will be from 250 to 360° C. The particular operating conditions are selected based upon the composition of the residue stream and are routinely determinable by persons of ordinary skill in the relevant art.

Once vaporized, the isobutyrate-containing components (i.e., α-MOB and β-MEMOB) of the vapor feed stream are converted in the presence of the catalyst to additional MMA.

The reaction step of the process comprises contacting a vapor feed stream from the vaporizing step with a catalyst under reaction conditions sufficient to convert by-products such as, for example, α-MOB, β-MEMOB, MAA and β-MOB, to additional MMA and produce a converted mixture that comprises MMA, MAA, $C_1$-$C_{12}$ alkyl alcohol, and water. In one embodiment of the invention, the aforesaid catalytic conversion is performed in the presence of methanol and/or a diluting agent such as an inert gas, at reaction temperatures of from about 200° C. to about 400° C., preferably from 250 to 360° C. The reaction pressure is not particularly limited, and normally is equal to or slightly above atmospheric pressure for convenience of operation.

The process of the invention employs a catalyst comprising at least one element selected from the group consisting of lithium, sodium, potassium, rubidium, cesium and francium. The element may be in any form suitable for use as a catalyst under the conditions in the reactor, e.g. it may be present as a compound of the element and another element. In one embodiment of the invention, the element of the catalyst may be present as a metal oxide, hydroxide or carbonate. The catalyst may also comprise, optionally, a promoter selected from the group consisting of P, B, Ti, Zn, Zr, Sn, Bi, Ce, alkaline earth metals, and mixtures thereof. The promoter may be in any form.

Furthermore, the catalyst preferably comprises a porous support material having pore openings greater than 1 nanometer. The porous support can be selected from a variety of commercially available inorganic carriers, such as silica gel, fumed silica, colloidal silica, alumina, titania, zirconia, in their pure forms, or in a combination of two or more. A silica gel type of material is preferred due to its weak acid-base property and high surface area. Some experimental samples such as mesoporous silica and foam silica like MCM-41, SBA-15, as disclosed in the literature (Nature, 1985, 318, 162; Science, 1998, 279, 548), can also be used.

The product mixture from the reaction step can be subjected to distillation to recover the product C1-C12 alkyl methacrylate together with some light by-products such as C1-C12 alkyl isobutyrate and methacrylonitrile. The distillate containing the product C1-C12 alkyl methacrylate can be recycled as desired to the process, e.g. to the separation and/or esterification steps.

One embodiment of the invention is a method for producing methacrylic acid esters comprising the steps of:
(1). hydrolyzing ACH with sulfuric acid to produce a hydrolysis mixture comprising 2-methacrylamide, α-sulfatoisobutyramide, α-hydroxyisobutyramide, and methacrylic acid;
(2). esterifying the hydrolysis mixture with a $C_1$-$C_{12}$ alkyl alcohol to produce an esterification mixture comprising a $C_1$-$C_{12}$ alkyl methacrylate, a $C_1$-$C_{12}$ alkyl α-hydroxyisobutyrate, and a $C_1$-$C_{12}$ alkyl β-$C_1$-$C_{12}$ alkoxyisobutyrate;
(3). separating the esterification mixture to produce an organic fraction comprising the $C_1$-$C_{12}$ alkyl methacrylate, the $C_1$-$C_{12}$ alkyl α-hydroxyisobutyrate and the $C_1$-$C_{12}$ alkyl β-$C_1$-$C_{12}$ alkoxyisobutyrate;
(4). separating the organic fraction to produce an enriched organic fraction comprising the $C_1$-$C_{12}$ alkyl methacrylate, the $C_1$-$C_{12}$ alkyl α-hydroxyisobutyrate and the $C_1$-$C_{12}$ alkyl β-$C_1$-$C_{12}$ alkoxyisobutyrate;
(5). flash distilling the enriched organic fraction to produce a vapor overhead stream comprising the $C_1$-$C_{12}$ alkyl methacrylate, the $C_1$-$C_{12}$ alkyl α-hydroxyisobutyrate and the $C_1$-$C_{12}$ alkyl β-$C_1$-$C_{12}$ alkoxyisobutyrate;
(6). condensing the vapor overhead stream to produce a vaporizer organic feed stream;
(7). providing a co-feed comprising a $C_1$-$C_{12}$ alkyl alcohol, which may or may not be the same alcohol as the $C_1$-$C_{12}$ alkyl alcohol used in the esterifying step (2);
(8). vaporizing the co-feed and at least a portion of the vaporizer organic feed stream to produce a vapor feed stream;
(9). contacting the vapor feed stream with a catalyst comprising at least one element selected from the group consisting of lithium, sodium, potassium, rubidium, cesium and francium, to convert the $C_1$-$C_{12}$ alkyl α-hydroxyisobutyrate and $C_1$-$C_{12}$ alkyl β-$C_1$-$C_{12}$ alkoxyisobutyrate to additional $C_1$-$C_{12}$ alkyl methacrylate and produce a converted mixture that comprises methacrylic acid, the $C_1$-$C_{12}$ alkyl methacrylate, $C_1$-$C_{12}$ alkyl alcohol, and water.

Preferably, the vapor feed stream comprises both the vaporized co-feed and the vaporizer organic feed stream. However, it is also possible to separately feed vaporized co-feed and vaporizer organic feed stream to the vaporizer. Preferably, the vapor feed stream contains less than 25 wt. %, total of MAM and MMA dimer (dimethyl 5-methyl-2-methyleneadipate), based on the weight of the vapor feed stream, excluding co-feed.

Preferably, the vapor feed stream contains less than 85 wt. % total of MAM and MMA dimer, based on the weight of MAM and MMA dimer in the stream fed to the flash distillation apparatus.

This embodiment includes a flash distillation as shown, e.g. in FIG. 3 in flash distillation apparatus 300. The flash distillation may be performed in any apparatus suitable for flash distilling process streams comprising the constituents discussed hereinabove. Suitable apparatus include, but are not limited to, flash drums, shell-and-tube heat exchangers, plate-and-frame heat exchangers, natural or forced circulation evaporators, wiped film evaporators, or combinations thereof. Suitable, but not limiting, conditions include operating pressures and temperatures in the respective ranges of 3.33–33.3 kPa (25-250 mmHg) and 100-200° C. Preferably, the pressure is kept as low as practical, such as 6.67 kPa (50 mmHg), to maintain a low corresponding temperature, such as less than or equal to 145° C. More preferably, the flash distillation pressure is in the range of 3.33–6.67 kPa (25-50 mm Hg) and the flash distillation temperature is maintained at less than 145 C. The vapor fraction may advantageously be from 0.1 to 1.0. The particular operating conditions are selected based upon the composition of the feed stream to the flash distillation and are routinely determinable by persons of ordinary skill in the relevant art to achieve the maximum recovery of desired components, while minimizing the heavies. In one embodiment of the invention, the flash distillation is a single stage flash distillation.

The bottoms stream from the flash distillation can be processed further, discarded as waste or burned as fuel.

Referring again to FIG. 3, this embodiment of the invention includes flash distillation apparatus 300. In a preferred embodiment, the flash distillation step is operated under conditions sufficient to maximize the recovery of $C_1$-$C_{12}$ alkyl α-hydroxyisobutyrate, $C_1$-$C_{12}$ alkyl beta-hydroxyisobutyrate, methacrylic acid and $C_1$-$C_{12}$ alkyl β-$C_1$-$C_{12}$ alkoxyisobutyrate, while minimizing the inclusion of methacrylamide and dimers such as, for example, dimethyl 5-methyl-2-methyleneadipate, in the flash overhead. For example, in one embodiment of the invention, a stream enriched in alpha-MOB, beta-MEMOB, beta-MOB, and MAA is obtained by a single-stage flash distillation of a residue stream and is subjected to the vapor phase catalytic reaction process described herein. The embodiment of the process that includes the flash distillation advantageously is operated in a manner that reduces fouling, reduces the buildup of heavy impurities in the recycle, reduces the organic fraction volume fed to the reactor and consequently the size of the reactor, and improves the energy efficiency and reliability of the product recovery process.

The mass yield of MMA can be calculated in two useful ways. For example, in the context of FIG. 3, the net gain of MMA obtained from the recovery reactor can be calculated based on either (1) the amount of the heavy residue stream 40 fed to the flash distillation apparatus or (2) the amount of distillate stream 60 fed to the reactor, as expressed in Equations (1) and (2), respectively.

$$Yres = \text{mass percent yield based on heavy residue stream} = (\text{mass MMA net gain})/(\text{mass residue}) * 100 \quad \text{Equation 1}$$

where "mass MMA net gain" is the mass of MMA in the reactor effluent minus the mass of MMA in the reactor feed stream and where, when the process includes a flash distillation apparatus, "mass residue" is the mass of all feed components to the flash distillation apparatus excluding MMA, and when the process does not include a flash distillation apparatus, "mass residue" is the mass of all feed components to the reactor excluding MMA and alkyl alcohol.

$$Y\text{flash} = \text{mass percent yield based on the mass of the condensed flash distillation overhead} = (\text{mass MMA net gain})/(\text{FLASH OVERHEAD})*100. \quad \text{Equation 2}$$

where "mass MMA net gain" is as defined above, and "FLASH OVERHEAD" is the mass of the condensed overhead stream from the flash distillation apparatus fed to the recovery reactor excluding alkyl alcohol and MMA.

Figure 6:
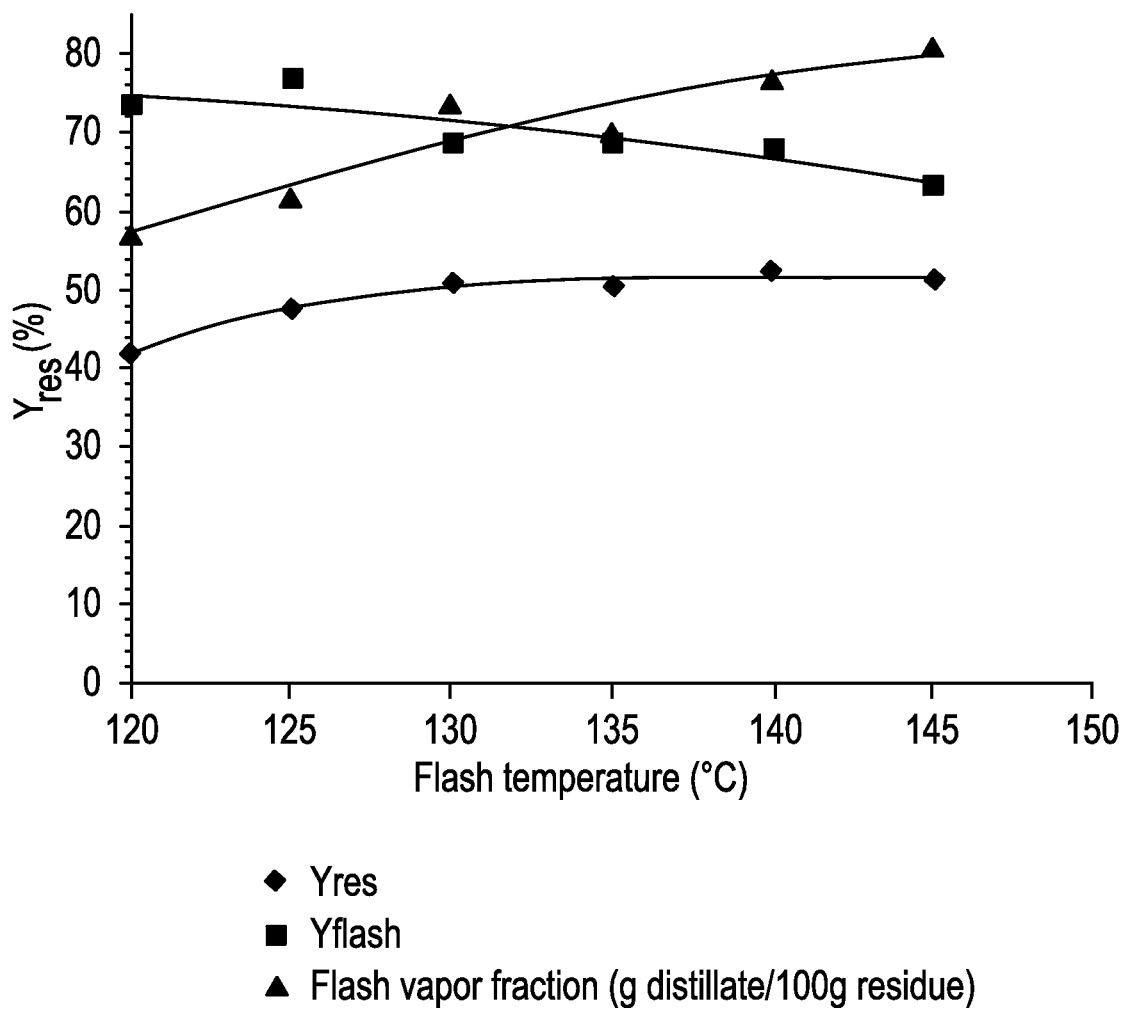
FIG. 6 is a graph showing data from Example 6, and includes a plot of Yres vs. flash distillation temperature, a plot of Yflash vs. flash distillation temperature, and a plot of flash vapor fraction vs. flash distillation temperature.

Equation 2 can be used to define a preferred flash distillation temperature. In one embodiment, for a given flash distillation pressure, a first process operating curve can be identified by plotting the amount of material vaporized (the flash vapor fraction) versus the flash distillation temperature. The flash vapor fraction is, for a given flash distillation pressure, the mass of the overhead stream of the flash distillation divided by the mass of material fed to the flash distillation. An example of this first process operating curve is shown in FIG. 6 and is labeled "flash vapor fraction"

A second process operating curve also can be identified for a given flash distillation pressure by plotting Yflash versus flash distillation temperature. An example of this curve, based on the process of FIG. 3, is shown in FIG. 6 and is labeled "yield on distillate feed." In one embodiment of the invention, the mass of the FLASH OVERHEAD in Equation 2 is determined based on the mass of stream 60, excluding alkyl alcohol and MMA, in FIG. 3.

Preferably, the flash distillation temperature is a temperature that is at or close to the flash distillation temperature where the first and second operating curves intersect, hereinafter referred to as the crossover temperature. In one embodiment of the invention, the flash distillation temperature is a temperature that is in the temperature range defined by the crossover temperature +/−10° C., preferably +/−5° C.

A third process operating curve can also identified in which, for a given flash distillation pressure, Yres is plotted versus flash distillation temperature. In one embodiment of the invention, the mass residue of Equation 2 is determined based on the mass of stream 40, excluding alkyl alcohol and MMA, in FIG. 3.

As can be seen from FIG. 6, the third curve surprisingly shows that raising the flash distillation temperature beyond the crossover temperature does not substantially improve the yield, expressed as Yres.

The following are potential benefits, in addition to the benefits mentioned hereinabove, that may be achieved while maximizing MMA recovery:

Recycle volume of unconvertible heavies may be minimized.

Feed rate of the methanol additive to the recovery reaction may be minimized. (Methanol amount is set relative to the flash distillate rate.)

Energy consumption may be minimized for affected unit operations, especially those within the recovery recycle loop, and especially separations steps.

Mild flash conditions may be maintained for better reliability, e.g. there is a reduced tendency for polymer fouling at lower flash temperatures.

The following examples illustrate the present invention in greater detail. They are not intended to limit the invention in any way.

EXAMPLES

Example 1

Preparation of 10% $Cs_2O/SiO_2$ (Davisil® 646) Catalyst

Cesium acetate aqueous solution was prepared by dissolving 2.72 grams of cesium acetate in 75 grams of deionized water. This aqueous solution was then added into a round bottom flask containing 18 grams of silica gel having pore size of 150 angstrom (Davisil® Grade 646 silica gel commercially available from Aldrich). The mixture was stirred for 10 minutes and then subjected to rotary evaporation under vacuum to remove the water. The powder was further dried in a vacuum oven at room temperature overnight, followed by drying at 120° C. for 4 hours and calcining at 450° C. for 5 hours in a box furnace under air atmosphere. The calcined powder contained a nominal 10 wt. % of $Cs_2O$ and was designated 10% $Cs_2O/SiO_2$ (Davisil® 646). It was then pressed and sieved into 14-20 mesh particles prior to being loaded into a fixed bed reactor for catalytic performance evaluation.

Example 2

Direct Conversion of MMA Purification Residue to MMA Over 10% $Cs_2O/SiO_2$ (Davisil® 646) Catalyst in the Presence of Methanol Three grams of 10% $Cs_2O/SiO_2$ (Davisil® 646) from Example 1 was loaded into the middle of a ½" O.D. stainless steel tube reactor with inert silicon carbide particles loaded below and above catalyst layer. The reactor tube was installed in an electrically heated clamshell furnace. The catalyst was pretreated in-situ by flowing 40 sccm $N_2$ at 365° C. for 18 hours and then cooled down to 310° C. for reaction.

An MMA distillation residue containing 0.19 wt. % MMA, 28.94 wt. % α-MOB, 12.57 wt. % β-MEMOB, 3.03 wt. % β-MOB, 10.84 wt. % MAA, 3.42 wt. % MAM, and 13.99 wt. % of 5-methyl-2-methylene adipate (MMA dimer), with the balance of content unknown, was obtained from a commercial process stream of the conventional ACH route to MMA. Compositional analysis was by gas chromatography.

A reaction feed was prepared from about 60 parts by weight of this MMA distillation residue and about 40 parts methanol. The feed composition was 41.5 wt. % methanol, 0.1 wt. % MMA, 19.1 wt. % α-MOB, 8.4 wt. % β-MEMOB, 2.0 wt. % β-MOB, 7.2 wt. % MAA, 2.3 wt. % MAM, and 9.4 wt. % MMA Dimer, with the balance of content unknown. The reaction feed was delivered as a liquid to the reactor at a rate of 3.0 g/hr along with a $N_2$ co-feed of 6 sccm. The combined feed was preheated to about 190° C. before entering the reactor tube. The feed vaporized in the reactor prior to reaching the catalyst bed.

The reactor effluent was passed through two consecutive cold traps to collect condensable products. The first trap was submerged in an ice water bath, and the second trap was submerged in a dry ice and isopropanol bath. The first trap was the main trap, and over 95 wt. % of the total condensable liquids were collected. Noncondensable effluent from the second trap was analyzed by an on-line gas chromatograph. The liquid products were weighed and also analyzed by gas chromatography.

The mass-based yield of MMA obtained from the reaction was calculated using Equation 1.

Figure 4:
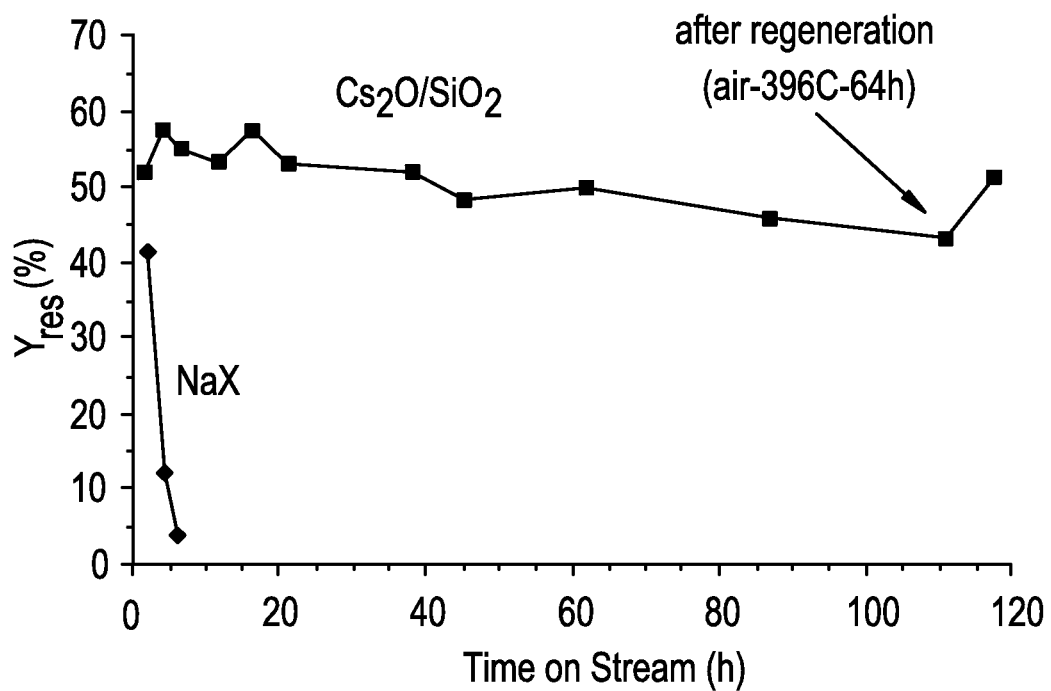
FIG. 4 is a graph showing data from Example 4 and Comparative Experiment 2 plotting Yres vs. time.

The MMA yield observed with time on stream is presented in FIG. 4.

An initial yield of 53-57% dropped gradually to about 43% in 110 hr. A regeneration step employing 40 sccm air at 396° C. for 64 hours restored performance to about 51% yield.

As will be recognized by persons of ordinary skill in the relevant art, providing an alkyl alcohol co-feed to the vapor feed stream to the reaction step would be expected to disfavor demethanolation of the β-MEMOB to MMA. Nonetheless, it has been surprisingly found that the aforesaid catalysts employed in the present invention successfully facilitate the concurrent conversion of $C_1$-$C_{12}$ alkyl α-hydroxyisobutyrate and $C_1$-$C_{12}$ alkyl β-$C_1$-$C_{12}$ alkoxyisobutyrate to additional $C_1$-$C_{12}$ alkyl methacrylate product. Another advantage is that the aforesaid catalysts are relatively insensitive to the presence of carboxylic acids, such as MAA. It is noted that previous technologies have not demonstrated efficacy in achieving simultaneous dehydration and demethanolation, more specifically, when methanol or another alkyl alcohol is added to prevent ester hydrolysis.

Comparative Experiment 1

Preparation of NaX catalyst

Fifty grams of sodium ion-exchanged zeolite X (NaX) was obtained from Aldrich (Molecular sieves 13X) and washed with deionized water three times with 500 grams of deionized water (1500 g water used in total). The washed zeolite was dried at 120° C. for more than 12 hours and then pressed and sieved into 14-20 mesh particles prior to being loaded into tubular reactor of the design used in Example 2.

Comparative Experiment 2

Direct Conversion of MMA Purification Residue to MMA Over NaX Catalyst in the Presence of Methanol Similar to the test conditions in Example 2, 3.0 grams of NaX was used instead of 3.0 grams of 10% $Cs_2O/SiO_2$ (Davisil® 646). The catalyst was pretreated in-situ by flowing 40 sccm air at 410° C. for 19 hours and then cooled down under 40 sccm $N_2$ flow to 250° C. for reaction.

Figure 5:
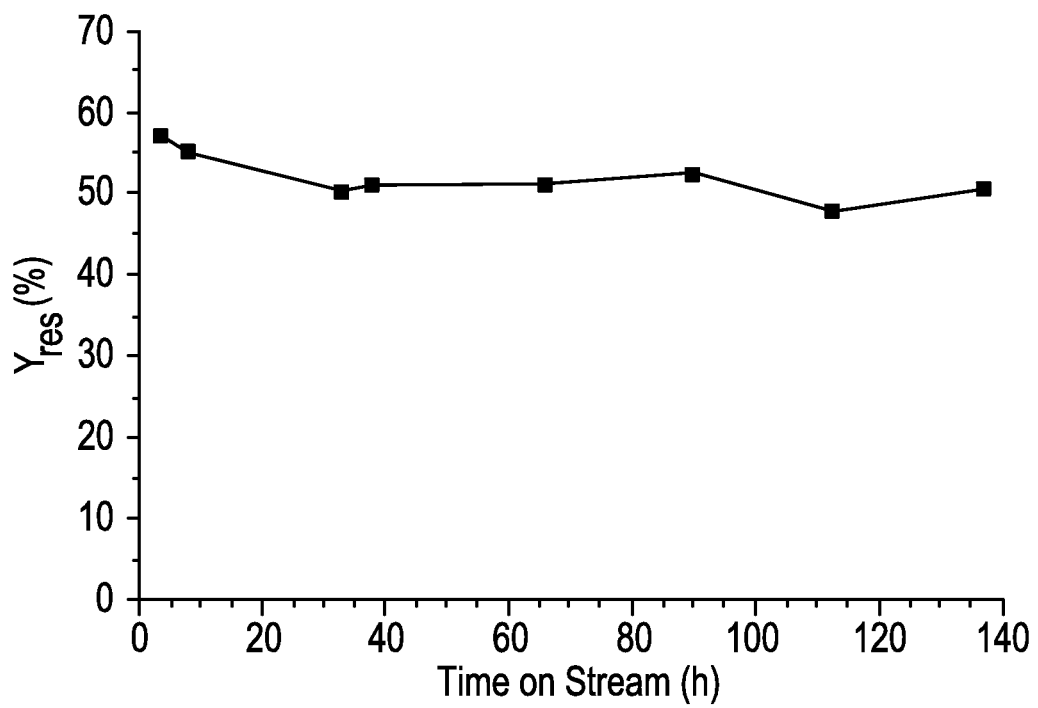
FIG. 5 is a graph showing data from Example 5 plotting Yres vs. time.

The MMA yield observed with time on stream is presented in FIG. 5. Yield dropped rapidly in four hours from 41% to 4%.

Example 3

Preparation of 10% $Cs_2O/SiO_2$ (Davisil® 636) Catalyst

The procedure of Example 1 was repeated except that the silica gel was (Davisil® Grade 636 silica gel commercially available from Aldrich).

Example 4

Direct Treatment of MMA Purification Residue Over 10% $Cs_2O/SiO_2$ (Davisil® 636) Catalyst in the Presence of Methanol and MMA Three grams of 10% $Cs_2O/SiO_2$ (Davisil® 636) from Example 3 was loaded similarly as in Example 2. The catalyst was pretreated in-situ by flowing 40 sccm $N_2$ at 372° C. for 16 hours and then cooled down to ca. 270° C. for reaction.

An MMA distillation residue containing 60.45 wt. % MMA, 15.96 wt. % α-MOB, 4.30 wt. % β-MEMOB, 1.10 wt. % β-MOB, 3.68 wt. % MAA, 3.02 wt. % MAM, and 5.69 wt. % MMA dimer, with the balance of content unknown, was obtained from a commercial process stream of the conventional ACH route to MMA.

A reaction feed was made by mixing about 77.8 parts by weight of this MMA distillation residue and about 22.2 parts methanol. This feed by gas chromatography analysis was 23.74 wt. % methanol, 46.8 wt. % MMA, 12.26 wt. % α-MOB, 3.32 wt. % β-MEMOB, 0.854 wt. % β-MOB, 2.83 wt. % MAA, 2.3 wt. % MAM, and 4.41 wt. % MMA dimer, with the balance of content unknown.

The reaction feed was delivered as a liquid to the reactor at a rate of 3.0 g/hr along with a $N_2$ co-feed of 6 sccm. The combined feed was preheated to about 180° C. before entering the reactor tube. The feed vaporized in the reactor prior to reaching the catalyst bed.

The reactor effluent was collected and analyzed and yield measured by the same methods as for Example 2.

The MMA concentration in the reactor product increased relative to the feed, and correspondingly, the concentrations of α-MOB, β-MEMOB, β-MOB, MAA, MAM, and MMA dimer were reduced. Mass MMA net gain approached 61 grams for every 100 grams of purification residue fed to the reactor. The compositions of the feed and product streams collected at different reaction temperatures are listed in Table 1.

TABLE 1

Composition of the feed and product streams and mass
MMA net gain for Example 4

| Component | Feed (wt. %) | Product (wt. %) | | | |
|---|---|---|---|---|---|
| | | 270° C. | 284° C. | 295° C. | 300° C. |
| methanol | 23.74 | 23.2 | 23.66 | 24.71 | 24.76 |
| MMA | 46.8 | 55.7 | 63.3 | 65.73 | 66.2 |
| methyl isobutyrate | 0 | 0.01 | 0.04 | 0.096 | 0.13 |
| α-MOB | 12.26 | 8.09 | 1.6 | 0.047 | 0.03 |
| β-MEMOB | 3.32 | 2.86 | 1.45 | 0.303 | 0.195 |
| β-MOB | 0.854 | 0 | 0.027 | 0.03 | 0.03 |
| MAA | 2.83 | 0.914 | 0.896 | 0.798 | 0.735 |
| MAM | 2.3 | 1.58 | 0.441 | 0.081 | 0.07 |
| MMA Dimer | 4.41 | 4.88 | 3.8 | 1.48 | 0.753 |
| Mass balance* (%) | — | 101 | 100.4 | 101.3 | 101.7 |
| $Y_{res}$ (%) | — | 24.3 | 49.1 | 60.9 | 58.9 |

*weight of product collected/weight of the feed delivered

Example 5

Direct Treatment of MMA Purification Residue Over
10% $Cs_2O/SiO_2$ (Davisil® 636) Catalyst in the
Presence of Methanol Three grams of 10% $Cs_2O/SiO_2$ (Davisil® 636) from Example 3 was loaded similarly as in Example 2. The catalyst was pretreated in-situ by flowing 40 sccm $N_2$ at 372° C. for 16 hours and then cooled down to 315° C. for reaction.

An MMA distillation residue containing 4.00 wt. % MMA, 34.62 wt. % α-MOB, 10.66 wt. % β-MEMOB, 2.35 wt. % β-MOB, 8.57 wt. % MAA, 3.84 wt. % MAM, and 15.58 wt. % MMA dimer, with the balance of content unknown, was obtained from a commercial process stream of the conventional ACH route to MMA.

A reaction feed was made by mixing about 60 parts by weight of this MMA distillation residue and about 40 parts methanol. This feed by gas chromatography analysis was 39.69 wt. % methanol, 1.61 wt. % MMA, 21.57 wt. % α-MOB, 6.58 wt. % β-MEMOB, 1.495 wt. % β-MOB, 5.74 wt. % MAA, 2.55 wt. % MAM, and 10.36 wt. % MMA dimer, with the balance of content unknown.

The reaction feed was delivered as a liquid to the reactor at a rate of 3.0 g/hr. No $N_2$ co-feed was used. The feed vaporized in the reactor prior to reaching the catalyst bed.

The reactor effluent was collected and analyzed and yield measured by the same methods as for Example 2.

An initial yield of 55-57% was obtained, which degraded with time on stream. The yield over time is shown in FIG. 5.

Example 6

Single-Stage Flash Distillation of MMA Purification
Residue and Catalytic Treatment of Flash Distillate
Using the 10% $Cs_2O/SiO_2$ (Davisil® 636) Catalyst An MMA distillation residue was obtained from a commercial process stream of the conventional ACH route to MMA. The residue contained 0.1 wt. % MMA, 36.9 wt. % α-MOB, 11.0 wt. % β-MEMOB, 2.7 wt. % β-MOB, 9.6 wt. % MAA, 6.9 wt. % MAM, and 16.6 wt. % MMA dimer, with the balance uncharacterized heavy ends.

The residue was processed by continuous-flow, single stage flash distillation using a laboratory apparatus comprising a glassware still pot and a 316 stainless steel, steam heated, forced recirculation reboiler. A residue feed rate of ca. 300 g/hr was fed along with an inhibitor feed of ca. 6 g/hr. The inhibitor feed was 99 wt. % MMA and 1 wt. % phenothiazine. The still pot pressure was 6.67 kPa (50 mmHg absolute). Individual and separate example experiments were performed for flash temperatures of 120, 125, 130, 135, 140, and 145° C.

Distillate from each flash experiment was condensed and then processed by a vapor phase reaction employing the 10% $Cs_2O/SiO_2$ (Davisil® 636) catalyst from Example 1. A reaction feed mixture was prepared by mixing 50 parts by weight of distillate and 50 parts methanol. For conducting the reaction, a neat 1.5 g catalyst bed was loaded into the center of a ½" O.D. vertically oriented stainless steel tube reactor with inert silicon carbide particles loaded below and above the catalyst bed. The catalyst was pretreated in-situ by flowing 40 sccm $N_2$ at 365° C. for 18 hours and then cooled to ca. 300° C. for reaction. The reaction feed was delivered as a liquid to the reactor at a rate of 1.5 g/hr. The feed vaporized in the reactor prior to reaching the catalyst bed. The reaction temperature was slowly raised until the conversions of α-MOB and β-MEMOB were above 90%.

Reactor product collection was accomplished by passing the reactor effluent through a cold trap submerged in an ice water bath. The liquid products were weighed and then analyzed by gas chromatography using capillary columns connected in sequence (Column 1: Restek Rtx-1, dimensions 30 m length×0.53 mm ID×1 μm film thickness; Column 2: Agilent DB-FFAP, dimensions 10 m length×0.53 mm ID×1 μm film thickness) and a flame ionization detector.

The post-reaction mass-based yield of MMA was calculated on the basis of residue fed to the flash (Eq. 1) and on the basis of flash distillate fed to the reaction (Eq. 2). The results are shown in FIG. 6.

As shown in FIG. 6, the yield on residue feed (Yres) increased with temperature up to about 130° C. For the higher temperatures investigated, yield on residue feed remained essentially constant.

Example 7

Distillation of MMA Purification Residue for
α-MOB/β-MEMOB Recovery and Dehydration of
the Distillate Stream Over 10% $Cs_2O/SiO_2$ (Davisil®
636) Catalyst in the Presence of Methanol An MMA distillation residue containing 0.51 wt. % MMA, 38.22 wt. % α-MOB, 13.66 wt. % β-MEMOB, 1.48 wt. % β-MOB, 7.10 wt. % MAA, 3.40 wt. % MAM, and 11.56 wt. % MMA dimer, with the balance of content unknown, was obtained from a commercial process stream of the conventional ACH route to MMA. An 8119 g quantity of this residue was distilled to produce 4059 g distillate containing 0.95 wt. % MMA, 75.5 wt. % α-MOB, 20.4 wt. % β-MEMOB and 0.01 wt. % of MAA. The distillation was achieved via continuous-flow fractional distillation using a 20-tray Oldershaw column. Reboiler and condenser pressures were respectively about 20.0 and 17.87 kPa (150 and 134 mmHg).

A reaction feed was prepared by mixing 60 parts by weight distillate with 40 parts methanol. The resulting feed mixture by gas chromatography analysis contained 40.79 wt. % methanol, 1.24 wt. % MMA, 44.94 wt. % α-MOB, 12.1 wt. % β-MEMOB, and 0.0078 wt. % MAA.

3.0 grams of 10% $Cs_2O/SiO_2$ (Davisil® 636) from Example 3 was loaded similarly as in Example 2. The catalyst was pretreated in-situ by flowing 40 sccm $N_2$ at 372° C. for 16 hours and then cooled down to 266° C. for reaction.

The reaction feed was delivered as a liquid to the reactor at a rate of 1.5 g/hr. No N₂ co-feed was used. The feed vaporized in the reactor prior to reaching the catalyst bed. Reaction temperature was raised until α-MOB and β-MEMOB conversions reached percentiles in the high 90's.

The reactor effluent was collected and analyzed and yield measured by the same methods as for Example 2, except that the net MMA gain was the difference between the reactor product and the starting MMA distillation residue.

The reaction temperature was slowly raised to get conversions of α-MOB and β-MEMOB in the high 90%. The mass-based yield of MMA was determined in the same manner as for Example 2, where "purification residue" was the sum of original purification residue excluding MMA where α-MOB/β-MEMOB distillate derived. For 100 grams of original purification residue, 37.6 grams of net MMA gain was achieved initially.

Example 8

Evaluation of 10% Cs₂O/SiO₂ (Davisil 636) Catalyst

Three grams of the catalyst of Example 3, was loaded into the middle of a ½" O.D. stainless steel plug flow tubular reactor with silicon carbide inert particles loaded above and below the catalyst charge. The reactor tube was installed in an electrically heated clamshell furnace. The catalyst bed was pretreated in situ by flowing 40 sccm N₂ at 300° C.-370° C. and 1 atmosphere pressure (atm) for 16-20 hours and then cooled to the reaction temperature, typically 200° C.-330° C., also at 1 atm.

Two feed compositions, shown in Table 2 as Feeds A and B, were employed individually. Each feed (as a single liquid mixture) was provided at a rate of 1.5-3.0 g/hr via syringe pump along with a co-feed of 6 SCCM N₂. The feed was vaporized, combined with the co-feed, and preheated to about 160° C.-180° C. before entering the reactor tube. Feed "A" also included 15 ppm of 4-methoxy phenol as inhibitor.

TABLE 2

Reactor feed compositions of Ex. 8

| Feed | α-MOB | β-MEMOB | MMA | MAA | methanol |
|---|---|---|---|---|---|
| | | | Component (wt. %) | | |
| A | 45.39 | 16.35 | 0.83 | 0.04 | 39.12 |
| B | 24.58 | 11.12 | 6.47 | 1.09 | 50.03 |

Reactor temperature and feed rate were varied to manipulate conversion. The single, vapor-phase reactor effluent was swept through a cold trap submerged in an ice water bath to collect condensable products, which were weighed.

Feed and product stream compositions were measured by gas chromatography using two capillary columns connected in sequence (Column 1: Restek Rtx-1, dimensions 30 meters length×0.53 millimeters ID×1 micrometer (μm) film thickness; Column 2: Agilent DB-FFAP, dimensions 10 m length× 0.53 mm ID×1 μm film thickness) and a flame ionization detector. Reaction product vapor exiting the cold trap was analyzed using a gas chromatograph equipped with silica gel and molecular sieve columns and a thermal conductivity detector. The conversions of α-MOB and β-MEMOB were calculated by difference as follows, where $n_i$ denotes the molar flow rate of species i:

$$\alpha - MOB \text{ conversion } (\%) = 100 \times \left(1 - \frac{n_{\alpha MOB}^{out}}{n_{\alpha MOB}^{in}}\right)$$

$$\beta - MEMOB \text{ conversion } (\%) = 100 \times \left(1 - \frac{n_{\beta MEMOB}^{out}}{n_{\beta MEMOB}^{in}}\right)$$

The combined molar yield of MMA and MAA on the sum of α-MOB and β-MEMOB fed was calculated as follows:

$$MMA + MAA \text{ yield } (\%) = 100 \times \frac{(n_{MMA}^{out} - n_{MMA}^{in}) + (n_{MAA}^{out} - n_{MAA}^{in})}{n_{\alpha MOB}^{in} + n_{\beta MEMOB}^{in}}$$

Test results obtained during the first 20 hours time on stream are shown, along with specific reaction conditions, in Table 3. In addition to conversion and yield, the relative molar ratio of by-product methyl isobutyrate (MIB) to MMA is shown.

Example 9

Preparation and Evaluation of 10% Cs₂O/SiO₂ (Merck 10181) Catalyst

The catalyst preparation of Example 8 was repeated except that Merck® Grade 10181 (from Aldrich) was used as the silica gel. The resulting calcined powder contained a nominal 10 wt. % of Cs₂O and was then pressed and sieved into 14-20 mesh size particles. It was designated 10% Cs₂O/SiO₂ (Merck® 10181). Performance was evaluated as described in Example 8 and according to the specific reaction conditions specified in Table 3.

Example 10

Preparation and Evaluation of 10% Cs₂O/SiO₂ (Aerosil 200) Catalyst

Cesium acetate aqueous solution was prepared by dissolving 2.72 g cesium acetate in 50 g deionized water. The aqueous solution was then added into a round bottom flask containing 18 g Aerosil® 200 fumed silica (commercially available from Evonik Industries, located in Calvert City, Ky., USA). Additional water (~200 g) was added to the flask to form a paste, which was then subjected to rotary evaporation under vacuum to remove the water. The resulting powder was further dried in a vacuum oven at room temperature overnight, followed by drying at 120° C. for 4 hours and calcination at 450° C. for 5 hours in a box furnace under air atmosphere. The calcined powder contained a nominal 10 wt. % of Cs₂O and was pressed and sieved into 14-20 mesh size particles. It was designated 10% Cs₂O/SiO₂ (Aerosil® 200). Performance was evaluated as described in Example 8 and according to the specific reaction conditions specified in Table 3.

Example 11

Preparation and Evaluation of 10% Cs₂O/1.7% P/SiO₂ (Davisil 646) Catalyst

A cesium acetate aqueous solution was prepared by dissolving 2.72 g cesium acetate in 75 g deionized water. This solution was then added into a round bottom flask containing 18 g silica gel (Davisil® Grade 646 from Aldrich). The mixture was stirred for 10 minutes, followed by the addition of 1.50 g $(NH_4)_2HPO_4$ and rotary evaporation under vacuum to remove the water. The resulting powder was further dried in a vacuum oven at room temperature overnight, followed with drying at 120° C. for 4 hours and calcination at 450° C. for 5 hours in a box furnace under air atmosphere. It was then pressed and sieved into 14-20 mesh size particles and designated 10% $Cs_2O$/1.7% $P/SiO_2$ (Davisil® 646). Performance was evaluated as described in Example 8 and according to the specific reaction conditions specified in Table 3.

Example 12

Preparation and Evaluation of 0.75% $K_2O$/6.2% $TiO_2/SiO_2$ (Merck® 10181) Catalyst A slurry was formed by adding 0.28 g potassium hydroxide, 2.0 g titanium oxide, and 30 g silica gel (Merck® Grade 10181) into 100 ml water in a 500 ml flask. The mixture was stirred under heating from room temperature to 90° C. for around one hour (15 min. ramp followed by holding at 90° C.). The mixture, then a paste, was subjected to rotary evaporation under vacuum to remove the water. The resulting powder was further dried in a vacuum oven at 120° C. for 8 hours and then pressed and sieved to 14-20 mesh particles. The particles were calcined at 600° C. for 2 hours in a box furnace under air atmosphere. The calcined catalyst was designated 0.75% $K_2O$/6.2% $TiO_2/SiO_2$ (Merck® 10181) catalyst. Performance was evaluated as described in Example 8 and according to the specific reaction conditions specified in Table 3.

Comparative Experiment 3

Preparation and Evaluation of NaX Zeolite Catalyst

The catalyst of Comparative Experiment 1 was designated NaX catalyst for the purposes of this experiment. Its performance was evaluated as described in Example 8 and according to the specific reaction conditions specified in Table 3.

Comparative Experiment 4

Preparation and Evaluation of Cs—Ru—X Zeolite Catalyst

Sodium ion-exchanged zeolite X (13X Molecular Sieves from Aldrich), 30 g, was soaked overnight in a solution of 4.81 g cesium acetate in 100 g water. Water was removed from the mixture by rotary evaporation at 50° C. under vacuum. The resulting solid was dried at 110° C. for 6 hours followed by calcination at 500° C. for 3 hours in static air. The calcined powder was soaked overnight in a solution of 0.342 g $RuCl_3$ in 50 g ethanol. The ethanol was removed from the mixture by rotary evaporation at 50° C. under vacuum. The subsequent solid was dried at 110° C. for 3 hours and calcined at 500° C. for 3 hours in air. The material was pressed and sieved into 14-20 mesh particles and designated Cs—Ru—X catalyst. Performance was evaluated as described in Example 8 and according to the specific reaction conditions specified in Table 3.

Comparative Experiment 5

Preparation and Evaluation of 30% $NaH_2PO_4/SiO_2$ (Davisil® 636)

Silica gel (Davisil® Grade 636 from Aldrich), 14 g, was added to a solution of 34 g water and 6 g $NaH_2PO_4$. The mixture was stirred at room temperature and then subjected to rotary evaporation at room temperature under vacuum to remove the water. The resulting solid was dried at 120° C. for 2 hours. The powder-form catalyst was designated 30% $NaH_2PO_4/SiO_2$ (Davisil® 636). Performance was evaluated as described in Example 8 and according to the specific reaction conditions specified in Table 3.

Comparative Experiment 6

Preparation and Evaluation of 11.3% $BaO/SiO_2$ (Davisil® 646)

Barium nitrate aqueous solution was prepared by dissolving 4.36 g barium nitrate in 60 g deionized water. This solution was then added into a round bottom flask containing 20 g silica gel (Davisil® Grade 646 from Aldrich). The mixture was subjected to rotary evaporation under vacuum to remove the water. The resulting powder was further dried in a vacuum oven at room temperature overnight, followed with drying at 120° C. for 6 hours and calcination at 500° C. for 5 hours in a box furnace under air atmosphere. It was then pressed and sieved into 14-20 mesh particles and was designated 11.3% $BaO/SiO_2$ (Davisil® 646). Performance was evaluated as described in Example 8 and according to the specific reaction conditions specified in Table 3.

TABLE 3

Catalyst performance data

| Example | Conditions | | | Conversion (%) | | Yield (%) | MIB/MMA ($\times 10^3$) |
| --- | --- | --- | --- | --- | --- | --- | --- |
| | T (° C.) | Feed | WHSV ($h^{-1}$) | α-MOB | β-MEMOB | | |
| 8 | 297 | A | 1.0 | 49.6 | 38.3 | 42.5 | 2.38 |
| | 302 | A | 1.0 | 76.1 | 64.3 | 64.1 | 2.52 |
| | 311 | A | 1.0 | 98.9 | 97.5 | 91.7 | 2.08 |
| | 320 | A | 1.0 | 100.0 | 100.0 | 87.9 | 2.54 |
| 9 | 303 | A | 1.0 | 35.9 | 9.7 | 24.5 | 1.40 |
| | 312 | A | 1.0 | 59.4 | 33.5 | 47.8 | 1.14 |
| | 321 | A | 1.0 | 93.2 | 81.4 | 82.0 | 1.14 |
| | 325 | A | 1.0 | 99.7 | 99.3 | 90.7 | 1.47 |
| 10 | 294 | A | 1.0 | 34.5 | 25.8 | 27.8 | 2.03 |
| | 306 | A | 1.0 | 66.5 | 54.0 | 52.6 | 1.70 |
| | 317 | A | 1.0 | 99.4 | 100.0 | 86.8 | 2.27 |
| | 322 | A | 1.0 | 100.0 | 100.0 | 82.2 | 3.15 |
| 11 | 317 | A | 1.0 | 99.8 | 80.1 | 88.0 | 0.43 |
| | 327 | A | 1.0 | 100.0 | 95.5 | 96.1 | 1.12 |
| 12 | 325 | A | 1.0 | 78.5 | 37.7 | 60.9 | 4.40 |
| | 330 | A | 1.0 | 93.2 | 58.2 | 72.4 | 4.84 |
| CE 3 | 236 | A | 1.0 | 99.9 | 51.4 | 73.3 | 0.18 |
| | 249 | A | 1.0 | 99.9 | 100 | 73.8 | 0.18 |
| CE 4 | 223 | B | 0.51 | 96.2 | 11.9 | 78.2 | 4.51 |
| CE 5 | 296 | B | 0.53 | 65.0 | 20.0 | 39.6 | 2.97 |
| | 337 | B | 0.53 | 99.0 | 39.5 | 73.2 | 3.60 |
| CE 6 | 317 | A | 1.0 | 18.4 | 12.4 | 4.9 | 3.65 |
| | 327 | A | 1.0 | 20.6 | 7.5 | 6.7 | 3.67 |

It has been surprisingly found that the catalyst employed in the present invention successfully facilitates the concurrent conversion of $C_1$-$C_{12}$ alkyl α-hydroxyisobutyrate and $C_1$-$C_{12}$ alkyl β-$C_1$-$C_{12}$ alkoxyisobutyrate to additional $C_1$-$C_{12}$ alkyl methacrylate product.

In addition, the capability of the catalyst to simultaneously convert additional by-product species, such as MAA and $C_1$-$C_{12}$ alkyl β-hydroxyisobutyrate, to $C_1$-$C_{12}$ alkyl methacrylate product is unexpected as shown in Examples 2, 4, 5 and 6.

Furthermore, it has surprisingly been found that the other by-products and compounds present in the organic fraction do not substantially interfere with the activity of the catalyst in the vapor phase.

We claim:
1. A method for producing methacrylic acid esters comprising the steps of:
   d. providing a $C_1$-$C_{12}$ alkyl alcohol and an organic fraction comprising $C_1$-$C_{12}$ alkyl methacrylate, $C_1$-$C_{12}$ alkyl α-hydroxyisobutyrate and $C_1$-$C_{12}$ alkyl β-$C_1$-$C_{12}$ alkoxyisobutyrate;
   e. vaporizing at least a portion of the organic fraction and at least a portion of the $C_1$-$C_{12}$ alkyl alcohol;
   f. contacting the vaporized organic fraction and alcohol with a catalyst comprising at least one element selected from the group consisting of lithium, sodium, potassium, and cesium, to convert the $C_1$-$C_{12}$ alkyl α-hydroxyisobutyrate and $C_1$-$C_{12}$ alkyl β-$C_1$-$C_{12}$ alkoxyisobutyrate to additional $C_1$-$C_{12}$ alkyl methacrylate and produce a converted mixture that comprises a $C_1$-$C_{12}$ alkyl methacrylate, methacrylic acid, $C_1$-$C_{12}$ alkyl alcohol, and water, wherein the element of the catalyst is present as a metal oxide, hydroxide or carbonate.

2. The method of claim 1 wherein the organic fraction is produced by a process comprising the steps of:
   a. hydrolyzing ACH with sulfuric acid to produce a hydrolysis mixture comprising 2-methacrylamide, α-sulfatoisobutyramide, α-hydroxyisobutyramide, and methacrylic acid;
   b. esterifying the hydrolysis mixture with a $C_1$-$C_{12}$ alkyl alcohol to produce an esterification mixture comprising a $C_1$-$C_{12}$ alkyl methacrylate, a $C_1$-$C_{12}$ alkyl α-hydroxyisobutyrate, and a $C_1$-$C_{12}$ alkyl β-$C_1$-$C_{12}$ alkoxyisobutyrate;
   c. separating the esterification mixture into an aqueous fraction and an organic fraction comprising the $C_1$-$C_{12}$ alkyl methacrylate, the $C_1$-$C_{12}$ alkyl α-hydroxyisobutyrate and the $C_1$-$C_{12}$ alkyl β-$C_1$-$C_{12}$ alkoxyisobutyrate.

3. The method of claim 2, further comprising the step of:
   g. recycling at least a portion of the converted mixture to one or more of steps (b) esterifying and (c) separating.

4. The method of claim 1, wherein the organic fraction in step (d) comprises at least a portion of a bottoms stream that is produced by distillation of a stream comprising (1) primarily the $C_1$-$C_{12}$ alkyl methacrylate and (2) higher boiling compounds comprising the $C_1$-$C_{12}$ alkyl α-hydroxyisobutyrate and the $C_1$-$C_{12}$ alkyl β-$C_1$-$C_{12}$ alkoxyisobutyrate.

5. The method of claim 1, further comprising step (d2) that comprises flash distilling the organic fraction to separate it into a stripped heavy residue stream and a flash vapor overhead stream, then feeding at least a portion of the flash overhead stream to step (e) as the organic fraction.

6. The method of claim 5, wherein the flash distillation temperature is a temperature that is in the temperature range defined by the crossover temperature +/−10° C.

7. The method of claim 1 wherein the $C_1$-$C_{12}$ alkyl alcohol is methanol, the $C_1$-$C_{12}$ alkyl methacrylate is methyl methacrylate, the $C_1$-$C_{12}$ alkyl α-hydroxyisobutyrate is methyl α-hydroxyisobutyrate (α-MOB), and the $C_1$-$C_{12}$ alkyl β-$C_1$-$C_{12}$ alkoxyisobutyrate is methyl β-methoxyisobutyrate (β-MEMOB).

8. The method of claim 2, further comprising the step of heating the hydrolysis mixture to a temperature between 90° C. and 160° C. to convert the α-hydroxyisobutyramide to 2-methacrylamide and produce a cracked hydrolysis mixture that is provided to the esterifying step (b).

9. The method of claim 1, wherein the catalyst further comprises a porous support material having pore openings greater than 1 nanometer.

10. The method of claim 1, wherein the catalyst further comprises a promoter selected from the group consisting of phosphorous, boron, titanium, zinc, zirconium, tin, bismuth, cerium, alkaline earth metals, and combinations thereof.

11. The method of claim 5, wherein the flash distillation is performed in the pressure range of 25 to 50 mmHg absolute and in the temperature range of 120 to 150° C.

12. The method of claim 1, wherein the at least one element comprises cesium.

13. A method for producing methacrylic acid esters comprising the steps of:
   (1). hydrolyzing ACH with sulfuric acid to produce a hydrolysis mixture comprising 2-methacrylamide, α-sulfatoisobutyramide, α-hydroxyisobutyramide, and methacrylic acid;
   (2). esterifying the hydrolysis mixture with a $C_1$-$C_{12}$ alkyl alcohol to produce an esterification mixture comprising a $C_1$-$C_{12}$ alkyl methacrylate, a $C_1$-$C_{12}$ alkyl α-hydroxyisobutyrate, and a $C_1$-$C_{12}$ alkyl β-$C_1$-$C_{12}$ alkoxyisobutyrate;
   (3). separating the esterification mixture to produce an organic fraction comprising the $C_1$-$C_{12}$ alkyl methacrylate, the $C_1$-$C_{12}$ alkyl α-hydroxyisobutyrate and the $C_1$-$C_{12}$ alkyl β-$C_1$-$C_{12}$ alkoxyisobutyrate;
   (4). separating the organic fraction to produce an enriched organic fraction comprising the $C_1$-$C_{12}$ alkyl methacrylate, the $C_1$-$C_{12}$ alkyl α-hydroxyisobutyrate and the $C_1$-$C_{12}$ alkyl β-$C_1$-$C_{12}$ alkoxyisobutyrate;
   (5). flash distilling the enriched organic fraction to produce a vapor overhead stream comprising the $C_1$-$C_{12}$ alkyl methacrylate, the $C_1$-$C_{12}$ alkyl α-hydroxyisobutyrate and the $C_1$-$C_{12}$ alkyl β-$C_1$-$C_{12}$ alkoxyisobutyrate;
   (6). condensing the vapor overhead stream to produce a vaporizer organic feed stream;
   (7). providing a co-feed comprising a $C_1$-$C_{12}$ alkyl alcohol, which may or may not be the same alcohol as the $C_1$-$C_{12}$ alkyl alcohol used in the esterifying step (2);
   (8). vaporizing the co-feed and at least a portion of the vaporizer organic feed stream to produce a vapor feed stream;
   (9). contacting the vapor feed stream with a catalyst comprising at least one element selected from the group consisting of lithium, sodium, potassium, and cesium to convert the $C_1$-$C_{12}$ alkyl α-hydroxyisobutyrate and $C_1$-$C_{12}$ alkyl β-$C_1$-$C_{12}$ alkoxyisobutyrate to additional $C_1$-$C_{12}$ alkyl methacrylate and produce a converted mixture that comprises methacrylic acid, the $C_1$-$C_{12}$ alkyl methacrylate, $C_1$-$C_{12}$ alkyl alcohol, and water, wherein the element of the catalyst is present as a metal oxide, hydroxide or carbonate.

14. The method of claim 13 wherein the $C_1$-$C_{12}$ alkyl alcohol is methanol, the $C_1$-$C_{12}$ alkyl methacrylate is methyl methacrylate, the $C_1$-$C_{12}$ alkyl α-hydroxyisobutyrate is methyl α-hydroxyisobutyrate (α-MOB), and the $C_1$-$C_{12}$ alkyl β-$C_1$-$C_{12}$ alkoxyisobutyrate is methyl β-methoxyisobutyrate (β-MEMOB).

15. The method of claim 13 wherein the vapor feed stream contains less than 85 wt. % total of MMA dimer (dimethyl 5-methyl-2-methyleneadipate) and MAM, based on the weight of MMA dimer and MAM in the stream fed to the flash distillation apparatus.

16. The method of claim 5 wherein the flash distillation temperature is a temperature that is in the temperature range defined by the crossover temperature +/−5° C.

17. The method of claim 1 wherein the catalyst comprises at least one element selected from the group consisting of potassium and cesium.

18. The method of claim 17 wherein the catalyst comprises cesium.

19. The method of claim 1 wherein the catalyst comprises an oxide, hydroxide or carbonate of cesium on a porous support material having pore openings greater than 1 nanometer.

20. The method of claim 19 wherein the support material comprises silica.

* * * * *